# (12) United States Patent
Howley et al.

(10) Patent No.: US 7,473,536 B2
(45) Date of Patent: Jan. 6, 2009

(54) ISOLATED AVIAN CELL THAT EXPRESSES VACCINIA VIRUS HOST RANGE GENES

(75) Inventors: Paul Howley, Vic (AU); Christine Meisinger-Henschel, Neuried (DE)

(73) Assignee: Bavarian Nordic A/S, Kvistgaard (DK)

( * ) Notice: Subject to any disclaimer, the term of this patent is extended or adjusted under 35 U.S.C. 154(b) by 47 days.

(21) Appl. No.: 10/524,043

(22) PCT Filed: Jul. 29, 2003

(86) PCT No.: PCT/EP03/08359

§ 371 (c)(1),
(2), (4) Date: Feb. 4, 2005

(87) PCT Pub. No.: WO2004/015118

PCT Pub. Date: Feb. 19, 2004

(65) Prior Publication Data

US 2006/0039928 A1 Feb. 23, 2006

(30) Foreign Application Priority Data

Aug. 7, 2002 (DK) ............................... 2002 01189

(51) Int. Cl.
A61K 39/12 (2006.01)
A61K 39/275 (2006.01)
C12P 1/00 (2006.01)
C12P 21/06 (2006.01)
C12P 21/04 (2006.01)
A61K 39/00 (2006.01)

(52) U.S. Cl. .................... 435/41; 435/69.1; 435/70.1; 424/199.1; 424/232.1

(58) Field of Classification Search .................. None
See application file for complete search history.

(56) References Cited

U.S. PATENT DOCUMENTS 5,494,807 A * 2/1996 Paoletti et al. ............. 435/69.3
5,833,975 A 11/1998 Paoletti et al.
6,004,777 A * 12/1999 Tartaglia et al. ............ 435/69.1
6,294,176 B1 * 9/2001 Cochran et al. .......... 424/199.1

FOREIGN PATENT DOCUMENTS

WO WO 98/40501 9/1998
WO WO 02/005668 7/2002

OTHER PUBLICATIONS

Fang et al., Expression of Vaccinia E3L and K3L Genes by a Novel Recombinant Canarypox HIV Vaccine Vector Enhances HIV-1 Pseudovirion Production and Inhibits Apoptosis in Human Cells, Virology, vol. 291:2, 272-284, 2001.*
Perkus et al., Vaccinia Virus Host Range Genes, 1990, Virology, vol. 179, pp. 276-286.*
Fields et al., Fields Virology, Third Edition, Chapter 83, p. 1642, vol. 2.*
Cardona et al., Characterization of a Recombinant Fowlpox Virus Expressing the Native Hexon of Hemorrhagic Enteritis Virus, 2001, Virus Genes, vol. 22, No. 3, pp. 353-361.*
Antoine et al., The Complete Genomic Sequence of the Modified Vaccinia Ankara Strain: Comparison with Other Orthopoxviruses, 1998, Virology, vol. 244, pp. 365-396.*
Dorlands Medical Dictionary, online, http://www.mercksource.com/pp/us/cns/cns_hl_dorlands_sp...=/ppdocs/us/common/dorlands/dorland/three/000032462.htm Viewed on Apr. 30, 2008.*
Baxby and Rondle, The Relative Sensitivity of Chick and Rabbit Tissues for the Titration of Vaccinia and Cowpox Viruses, 1967, Archives of Virology, pp. 263-267.*
Fowlpox Virus Host Range Restriction . . . By P. Somogy et al. (Virology 197, (1993).
Vaccinia Virus Host Range Genes by M. E. Perkus et al. (Virology 179 (1990).
Marker Rescue of the Host Range Restriction . . . by L.S. Wyatt et al. (Virology 251 (1998).
Host Range Restriction of Vaccinia Virus E3L . . . by E. Beattie et al. (Virus Genes 12:1, 1996).
Expression OPF Vaccinis E3L and K3L Genes . . . by Zhi Yu Fang et al. (Virology 291 (2001).

* cited by examiner

*Primary Examiner*—Bruce Campell
*Assistant Examiner*—Benjamin P Blumel
(74) *Attorney, Agent, or Firm*—Law Office of Salvatore Arrigo

(57) ABSTRACT

The invention concerns an Avipoxvirus comprising in the viral genome a Vaccinia virus host range gene or a homologue of said host range gene. The invention further relates to cells, preferably avian cells, comprising a Vaccinia virus host range gene or a homologue of said host range gene. Moreover the invention concerns the use of a Vaccinia virus host range gene or an homologue thereof to increase the titer of avipoxviruses produced from cells after infection of said cells with the avipoxvirus, wherein the host range gene is expressed in said cells.

14 Claims, 7 Drawing Sheets

Figure 1:
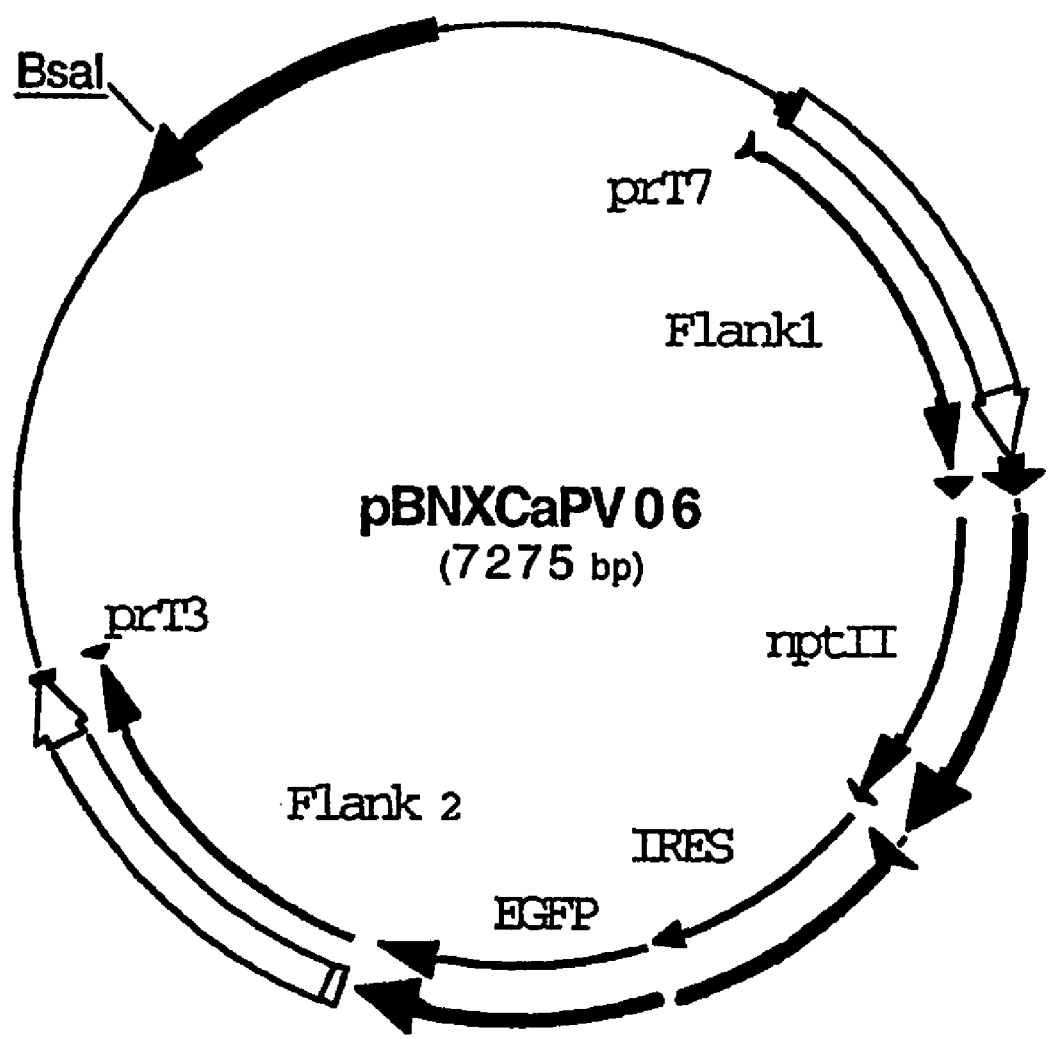

Figure 4:

attaataaactttaagacatgtgtgttatactaagatggttggcttattccatagtagcttgtggaatttata
taattatttgaaattctgtacacacaatatgattctaccaacgaataaggtatcatcgaacaccttaaatat estimated natural promoter sequence for C7L in MVA aacttatgatagtaaaactagtacccaatatgtaaagatgaaaaagtaaattactattaacgccgtcggtatt
ttgaatactatcatttttgatcatgggttatacatttctactttttcatttaatgataattgcggcagccataa cgttcatccattcagtatgggtatacagcacgaattcgacatcattattaatggagatatcgcgttgagaaat
gcaagtaggtaagtcatacccatatgtcgtgcttaagctgtagtaataattacctctatagcgcaactcttta
▸ M  G  I  Q  H  E  F  D  I  I  I  N  G  D  I  A  L  R  N ttacagttacataaagggga taactacggatgcaaactaaaaattatttcgaatgattacaagaaattaaagt
aatgtcaatgtatttccctattgatgcctacgttggattttaataaagcttactaatgttctttaatttca
▸L  Q  L  H  K  G  D  N  Y  G  C  K  L  K  I  I  S  N  D  Y  K  K  L  K ttagattcattatacgcccagattggtcggaaatcgacgaggtcaaaggattaacgtatttgcaaacaacta
aatctaagtaatatgcgggtctaaccagcctttagctgctccagttcctaattggcataaaacgttbgtggat
▸F  R  F  I  I  R  P  D  W  S  E  I  D  E  V  K  G  L  T  V  F  A  N  N  Y tgcggtgaaagttaataaggtagatgacacgttctattacgtaatatatgaggctgtaatacatctgtataac
acgccactttcaattattccatctactgtgcaagataatgcattatatactccgacattatgtagacatattg
▸ A  V  K  V  N  K  V  D  D  T  F  Y  Y  V  I  Y  E  A  V  I  H  L  Y  N

C7L gene from MVA aaaaaaacagagatattgattattctgatgatgagaacgaactctttaaacactattacccatacatcagtc
ttttttgtctctataactaaataagactactactcttgcttgagaaatttgtgataatgggtatgtagtcag
▸K  K  T  E  I  L  I  Y  S  D  D  E  N  E  L  F  K  H  Y  Y  P  Y  I  S taaatatgattagtaaaagtataaagttaaagaagaaaactactcatcccgtatataagaacatccgttaat
attatactaatcatttttcatatttcaatttcttctttgatgagtaggggcatatatctbgtaggcaatta
▸L  N  M  I  S  K  K  Y  K  V  K  E  E  N  Y  S  S  P  Y  I  E  H  P  L  I cccgtatagagattatgagtccatggattaa
gggcatatctctaatactcaggtacctaatt      (Seq. Id No:1)
▸ P  Y  R  D  Y  E  S  M  D  *

Figure 7A: (Seq ID No: 3)

ATACTATTCTTCACGGTACATTTAAAAAAAGGAATATAGTCAGAAACAGGAAATATACT
TTCACTATAACATGGTCTAATTTCGAATGTCCGACGTTAGGAGACGTTAAGTCTTCTTC
ACCTAATACCTGTAATAGAGTAGTTTTAGACGGTAGTAGATACGTTACAAAAACCTTTA
ATGATACAATATAAATGGAACTAACTAGAGAAACGCTGATATTTGTAGGCATTACTGTA
CTAGTAGTAGTAATGATCATATCTGGTTTCTCACTAATATTGCGATTGATACCTGGTGT
ATATTCATCAGTTATTAGATCGTCGTTCGTAGGAGGGAAAATATTAAGATTTATGGAGG
TATTCTCTACTGTTATGTTTATACCATCATTAGTAATACTTTATACAGCATATATAAGG
AAATCTAAAGTGAAAAATAACTAAATATTATAGTATTTGTAATAAATGGCTACTGGAGA
GATTCGTCTTATTATAGGGCCTATGTTTTCAGGTAAAACAACAGAATTAGTTAGATTAA
TAAGAAGATTTATGATATCGGGACGTAAATGTATAATAATAAAACATTGTAGTGATTCC
CGTTATACCGAAGGAGATTTAGAAGCTATATATACTCATGATAAAATTTCGATGGAAGC
ACTATCGTGTAGCAAATTATTACCTTTAATACCTAAAATTGATAACTTTGAAGTAATAG
GTATAGACGAAGGACAGTTTTTTGAAGATATAGTAGAATTTAGTGAGATTATGGCTAAT
AAGGGTAAAACTGTAATCATAGCGGCTTTAAATGGAGATTTCAAACGACAATTATTTGG
AAACATATTTAAACTATTATCTTTATCAGAATCAGTTACTAGTTTAACTGCTATTTGTG
CAGTTTGTAAAAACGAAGCATCTTTTTCTAAGCGCATGACTGATGATAAAGATGTAAAA
GTTATAGGAGGTAAAGAAATGTATACTGCTGTTTGTAGAAAATGCTTTTTATGAGTC

Figure 7B: (Seq. ID No: 4)

TAATATACGTACTAAATACTTGTACGTACAACTATGTTAGAATAATTTGCTTAGTATAG
TATATAAACAAGTATGTAAAAAATAAAATTGATATAAAAGTAGTCTTCTATTCCGAACA
ATAACTATACAAAATGGATTTAGATATTAAATCTTGCAGAAGTATTTACAAAATATGGG
ATAAATATCATTTTATGACAGGGTATAAATATAAAAATGATAAACAGAGATTTAAAATT
ACAATTTACTGTAAATGTGATTGTTCTATCAAAGAATATCCTTATAGATTGTTACTGA
GAAACTGCTTTTAATGTATATTATTAATAAGTTTAGAGGAAAGTATCTAATCAAAATTA
GGATAGAACCCATAGTTAAAAATTAAATCATATATCAATACATGTCAGTTTTTTATCGA
AAAATGGATTTATAAATAAAATGAAAAATAACTTGAATGAAGGAAAAAATAACCATGAG
TAAAAAACCAGTAAAGACGGTCCAGCGTAGACGTGGAAACGATGAGGATAATAAGTTTA
CTTGTATCCAAGCGCTAGAACATGCAAAAAGCTTATGTACTAAAAATAATAAAATAGTT
AAATCTGTTAAACTATCACAATCTCTCTTTAAGTCATCTAACAATATTTCTGTGATATT
AGAACCAGAATATAAAGACAAATTAGTGACTCCTCTTATTATTGTAGAAGGTGAAGGAA
AAATATACCATAATAAGAATGATAGTTTTAATCGTGAAGAACCGTATTTTCTAAAAATA
CGACCTACGTTAATGAATCCTATATTATATCAGATTATGGAATGCATTTATAGAGATCT
CAATTATTTGGATCCCGAGAATACGATGGATGAAAAAACATTTAAAGATTGTCATCTGT
ATATTAACGGAAATAGGATTATGTCCGCCGACGTAAAATATTTGAAGAATGGTAAACCT
GTAGGAGAAAAATTATCCGTATCCAAGGAAATAGATAAACTGGTTAAAAAAGATCCACA

US 7,473,536 B2

ISOLATED AVIAN CELL THAT EXPRESSES VACCINIA VIRUS HOST RANGE GENES

CROSS REFERENCE TO RELATED APPLICATIONS

This application is the U.S. national phase of PCT application PCT/EP2003/008359 filed 29 Jul. 2003 with a claim to the priority of PCT patent application PA200201189 itself filed 7 Aug. 2002.

The invention concerns an Avipoxvirus comprising in the viral genome a Vaccinia virus host range gene or a homologue of said host range gene. The invention further relates to cells, preferably avian cells, comprising a Vaccinia virus host range gene or a homologue of said host range gene. Moreover the invention concerns the use of a Vaccinia virus host range gene or an homologue thereof to increase the titer of avipoxviruses produced from cells after infection of said cells with the avipoxvirus, wherein the host range gene is expressed in said cells.

BACKGROUND OF THE INVENTION

The poxviridae comprise a large family of complex DNA viruses that replicate in the cytoplasm of vertebrate and invertebrate cells. The family of poxviridae can be divided into the subfamily chordopoxvirinae (vertebrate poxviruses) and entomopoxvirinae (insect poxviruses).

The chordopoxvirinae comprise several poxvirus species that can be used as vectors to express exogenous DNA segments encoding antigens against which an immune response is to be induced. Examples for poxviruses that can be used as live vaccines are Vaccinia virus and avipoxviruses, such as the canarypoxvirus and the fowlpoxvirus.

The use of Vaccinia viruses to engineer viral vectors for recombinant gene expression and for the potential use as recombinant live vaccines has been disclosed in numerous publications (see e.g. Mackett, M., Smith, G. L. and Moss, B. [1982] P.N.A.S. USA 79, 7415-7419; Smith, G. L., Mackett, M. and Moss, B. [1984] Biotechnology and Genetic Engineering Reviews 2, 383-407). To construct recombinant Vaccinia viruses, DNA sequences (genes), which code for foreign antigens are introduced into the genome of the Vaccinia virus under the regulation of suitable poxvirus promoters. If the gene is integrated at a site in the viral DNA, which is nonessential for the life cycle of the virus, the recombinant Vaccinia virus remains infectious. After infection the recombinant virus expresses the integrated DNA sequence (EP 83286 and EP 110385). The recombinant Vaccinia viruses prepared in this way can be used, on the one hand, as live vaccines for the prophylaxis of infectious diseases, and on the other hand, for the preparation of heterologous proteins in eukaryotic cells.

The use of Vaccinia virus as vector for the development of recombinant live vaccines has been affected by safety concerns and regulations. Most of the recombinant Vaccinia viruses described in the literature are based on the Western Reserve strain of Vaccinia virus. It is known that this strain has a high neurovirulence and is thus poorly suited for use in humans and animals (Morita et al., Vaccine 5, 65-70 [1987]). On the other hand the Modified Vaccinia virus Ankara (MVA) is known to be exceptionally safe. MVA has been generated by long-term serial passages of the Ankara strain of Vaccinia virus (CVA) on chicken embryo fibroblasts (for review see Mayr, A., Hochstein-Mintzel, V. and Stickl, H. [1975] Infection 3, 6-14; Swiss Patent No. 568392). MVA is distinguished by its great attenuation that is to say by diminished virulence or infectiosity while maintaining good immunogenicity. Recombinant MVA useful as vaccines have already been constructed and used in clinical trials. WO 98/13500 discloses a recombinant MVA containing and capable of expressing one or more DNA sequences encoding dengue virus antigens. The foreign DNA sequences were recombined into the viral DNA at the site of a naturally occurring deletion in the MVA genome.

Another approach towards the generation of safe and effective poxvirus vaccines utilizes avipoxviruses, e.g. canarypoxvirus and fowlpoxvirus, to express antigens to induce an immune response (U.S. Pat. No. 6,340,462). Avipoxviruses are naturally host-restricted and productively replicate only in avian species and cells (Taylor et al., Vaccine 1995, 13: 539-549). If human cells are infected with an avipoxvirus, heterologous genes are expressed from the viral genome. However, the avipoxvirus does not replicate in the human cells and there is, thus, no risk that the human being is harmed by productive virus replication. Various recombinant avipoxviruses have been constructed that express e.g. lentiviral gene products (U.S. Pat. No. 5,766,598), cytokines and/or tumor-associated antigens (U.S. Pat. No. 5,833,975) or rabies G glycoprotein (Taylor et al., Vaccine 1995, 13: 539-549). A recombinant canarypox virus expressing the four HIV genes gag, pol, env and nef has already been used in clinical trials (Peters, B. S., Vaccine 2002, 20: 688-705).

Since avipoxviruses productively replicate only in avian cells, these cells have to be used for the amplification of the virus and for the generation of recombinant viruses. Unfortunately, the titers of avipoxviruses obtained with avian cells are relatively low when compared to other poxviruses and it is, thus, more difficult to produce larger amounts of (recombinant) avipoxviruses in an industrial scale.

OBJECT OF THE INVENTION

It is the object of the present invention to provide means allowing the production of avipoxviruses, in particular recombinant avipoxviruses, at higher titers allowing the production of larger amounts of virus, in particular in an industrial scale.

DETAILED DESCRIPTION OF THE INVENTION

According to the present invention vaccinia virus host range genes are expressed in cells productively infected with an avipoxvirus. The expression of these vaccinia virus genes leads to an increase of the avipoxvirus titer produced from the infected cells. As it will be shown in more detail in the example section for a specific embodiment of the invention recombinant avipoxviruses, in particular a canarypoxvirus, expressing a Vaccinia virus host range gene, in particular the Vaccinia virus gene C7L, show a 10 fold increase of the viral titer on avian cells, in particular on Chicken Embryo Fibroblasts (CEF-cells) compared to the Avipoxvirus lacking the Vaccinia virus host range gene. Although the host range gene is expressed from the recombinant avipoxvirus, the growth on human cell lines is not affected, i.e. the Avipoxvirus expressing the Vaccinia virus host range gene is as attenuated as the Avipoxvirus not expressing the host range gene.

According to a preferred embodiment the invention concerns avipoxviruses comprising in the viral genome a Vaccinia virus host range gene or a homologue of said host range gene.

The term "avipoxvirus" refers to any avipoxvirus, such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus.

An example for a canarypox virus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of a Fowlpox virus are strains FP-1, FP-5 and TROVAC (U.S. Pat. No. 5,766,598). FP-1 is a Duvette strain modified to be used as a vaccine in one-day old chickens. The strain is a commercial fowlpox virus vaccine strain designated O DCEP 25/CEP67/2309 October 1980 and is available from Institute Merieux, Inc. FP-5 is a commercial fowlpox virus vaccine strain of chicken embryo origin available from American Scientific Laboratories (Division of Schering Corp.) Madison, Wis., United States Veterinary License No. 165, serial No. 30321.

The Vaccinia virus host range gene comprised in the viral genome of the avipoxvirus can be any host range gene. The term "Vaccinia virus host range gene" refers to a gene encoding a gene product, which is necessary that a Vaccinia virus is able to replicate on cells of species on which the virus does not replicate in the absence of the functional host range gene. If the respective host range gene is deleted the viral replication may be restricted to cells from only one animal species. By way of example reference is made to the Vaccinia virus genes K1L, C7L and E3L. It has been shown that the expression of either K1L or C7L allows vaccinia virus replication in human MRC-5 cells; the E3L gene was shown to be required for Vaccinia virus replication in monkey Vero and human HeLa cells (Wyatt et al., Virology 1998, 251: 334-342).

The term "Vaccinia virus host range gene for human cells" refers to genes that are required for the replication of the Vaccinia virus in human cells.

Examples for Vaccinia virus host range genes are the genes C18L, C17L, C7L, K1L, E3L, B4R, B23R and B24R according to the nomenclature as used in Johnson et al., Virology 1993, 196: 381-401 and genes (CHO)hr and SPI-1 as specified in Wyatt et al., Virology 1998, 251: 334-342. Preferred host range genes are the host range genes for human cells, e.g. E3L, K1L and C7L. Most preferred is C7L. The nucleotide sequence of the C7L gene of MVA with regulatory sequences is shown in FIG. 4 and as SEQ ID: No 1. The corresponding amino acid sequence is shown as SEQ ID: No 2.

The term "homologue of a host range gene" refers to a gene having a homology of at least 50%, preferably at least 70%, more preferably of at least 80%, most preferably of at least 90% in the coding part of the nucleotide sequence, wherein the "homologue of the host range gene" has the biological function of a host range gene. The biological function and definition of a host range gene is defined above. Specific tests how to determine whether a gene has the biological function of a host range gene are known to the person skilled in the art. In particular reference is made to Wyatt et al., Virology 1998, 251: 334-342, Perkus et al., Virology 1990, 179: 276-286 and Gillard et al., J. Virol. 1985, 53: 316-318.

According to the present invention the Vaccinia virus host range gene comprised in the viral genome of the Avipoxvirus is a functional gene. The term "functional gene" as used in the present application is to be interpreted in that the host range gene comprises regulatory elements that are functional in cells productively infected with an Avipoxvirus and that allow the generation of the functional gene product of the host range gene in said Avipoxvirus infected cells. Thus, the Vaccinia virus host range gene is expressed in the cells.

The term "cells, productively infected with an Avipoxvirus" refers to cells that allow the propagation of the Avipoxvirus and/or the generation of recombinant Avipoxviruses. The cells are preferably avian cells, most preferably CEF cells. Other preferred cells are the quail fibroblast cell line QT-35 (Cowen, B. S. and Braune, M. O., Avian Dis. 1988; 32: 282-297; Schnitzlein, W. M. et al., Virus Res. 1988; 10: 65-76) or canary embryo cells (Wurtz, S., Bonnet-Piro, E. and Barban, V., Poster P45 and Wurtz, S. and Barban, V., Poster P93, XIIIth International Poxvirus and Iridovirus Symposium, Montpellier, France, Sep. 2-6, 2000). Further, it is obvious for a person skilled in the art to try whether other, commercially available avian cell lines are suitable for the propagation of Avipoxviruses. Examples for such cell lines obtainable at the American Type Culture Collection (ATCC) are the quail fibroblast cell lines QT6 (ATCC CRL-1708), QM7 (ATCC CRL-1962), QNR/D (ATCC CRL-2532), the quail cell line QNR/K2 (ATCC CRL-2533), the duck fibroblast cell line Duck embryo (ATCC CCL-141), the turkey lymphoblast cell line MDTC-PR19 (ATCC CRL-8135), the chicken fibroblast cell lines SL-29 (ATCC CRL-1590) and UMNSAH/DF-1 (ATCC CRL-12203) and the chicken lymphoblast cell lines DT40 (ATCC CRL-2111) and DT95 (ATCC CRL-2112).

The regulatory elements comprise inter alia suitable promoter/enhancer and termination signals that are known to the person skilled in the art as being active in avipoxvirus infected avian cells. Examples for such promoter/enhancer elements are the Vaccinia virus promoters $P_{7.5}$, $P_{H5}$, $P_{11}$, a synthetic strong promoter $P_{syn}$ (see Genetically engineered viruses, edited by Ring, C. J. A. and Blair, E. D., Bios Scientific Publishers Ldt., 2001, Oxford, UK, ISBN 1 85996 103 7, chapter Vaccinia virus promoters, starting on page 110; Amano, H. et al., Virology 1999, 256: 280-290) as well as the autologous promoters of the Vaccinia virus host range genes.

Fang, Z.-Y. et al., (Virology 2001, 291: 272-284) discloses a recombinant canarypoxvirus that comprises in the viral genome three expression cassettes for HIV gag-pro, gp120/TM and a Nef/Pol poly-epitope string and an expression cassette of the E3L gene. The viral genome of said recombinant further comprises the Vaccinia Virus K3L gene. Due to the presence of the vaccinia virus E3L and K3L genes the apoptosis in infected HeLa cells was significantly reduced and the antigen production in the infected cells was enhanced. Fang et al., does not disclose that the Vaccinia virus host range gene is implicated in any increase of the titer of the recombinant avipoxvirus. Thus, the avipoxvirus according to the present invention is an avipoxvirus comprising in the viral genome a Vaccinia virus host range gene or a homologue of said host range gene, with the proviso that the host range gene is not the E3L gene if the avipoxvirus is a recombinant canarypoxvirus comprising in the viral genome expression cassettes for (I) HIV gag-pro, (II) gp120/TM and a (III) Nef/Pol poly-epitope string as well as for (IV) the Vaccinia virus K3L gene. According to a further alternative embodiment the invention concerns an avipoxvirus comprising in the viral genome a Vaccinia virus host range gene or a homologue of said host range gene, with the proviso that the host range gene is not the E3L gene if the avipoxvirus is a recombinant canarypoxvirus comprising in the viral genome the Vaccinia virus K3L gene.

The Vaccinia virus host range gene is preferably inserted into a non-essential region of the viral genome, into an intergenic region of the viral genome or into a deletion site of the viral genome. "Non essential regions" are regions that are not required for the replication of the viral genome in avian cells and not needed for the production of infectious viruses. Non-essential regions are known to the person skilled in the art and are disclosed i.a. in U.S. Pat. No. 5,766,598. The insertion of heterologous genes into the Canarypox virus thymidine kinase gene has been disclosed by Amano, H. et al. (Virology 1999, 256: 280-290).

Figure 3:
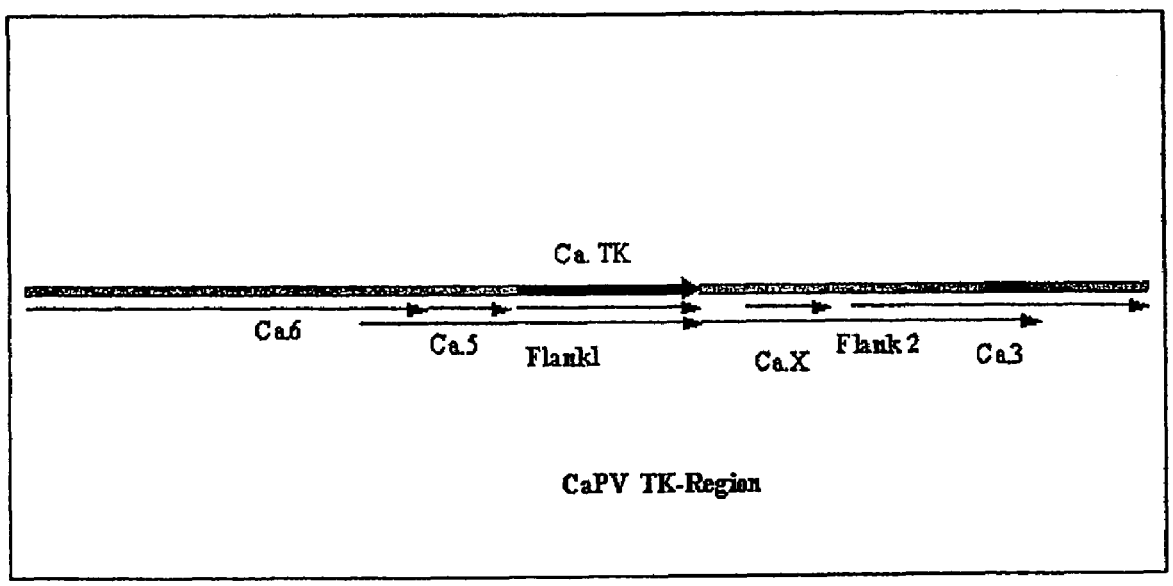

"Intergenic regions" in the viral regions are regions that do not contain coding sequences and preferably no regulatory elements. The location of intergenic regions is known to the person skilled in the art (see e.g. Alfonso C. L. et al., J. Virol 2000, 74: 3815-3831). An example for an insertion into an intergenic region is shown in FIG. 3 and in the examples section. Thus, it is a preferred embodiment, in particular for a Canarypoxvirus, to insert the host range gene into the intergenic region between the Tk gene and the adjacent X gene.

A deletion site is the part of the genome of a modified avipoxvirus that is deleted with respect to the parent avipoxvirus. Deletion sites may be generated by using methods known by a person skilled in the art, starting from a wild type avipoxvirus genome.

The Avipoxvirus comprising a Vaccinia virus host range gene may be a wild-type virus comprising as only heterologous gene the Vaccinia virus host range gene, an attenuated virus comprising as only heterologous gene the Vaccinia virus host range gene or a recombinant Avipoxvirus, i.e. a wild-type or attenuated virus comprising further heterologous genes in addition to the Vaccinia virus host range gene.

An "attenuated virus" is a virus originating from a pathogenic virus but that upon infection of the host organism leads to a lower mortality and/or morbidity compared to the non-attenuated parent virus. Examples of attenuated poxviruses are known to the person skilled in the art. Examples for attenuated Avipoxvirus strains are i.a. FP-1, ALVAC or TROVAC.

The term "recombinant virus" refers to any virus that comprises in addition to the vaccinia virus host range gene an additional heterologous nucleic acid that is not naturally part of the viral genome. A heterologous gene can be, e.g. a therapeutic gene, a gene coding for a peptide comprising at least one epitope to induce an immune response, an antisense expression cassette or a ribozyme gene.

Thus, according to a preferred embodiment the invention concerns Avipoxviruses comprising in the viral genome at least one heterologous nucleic acid sequence in addition to the sequence encoding the Vaccinia virus host range gene, wherein the additional heterologous nucleic acid sequence is preferably selected from a sequence coding for at least one antigen, antigenic epitope, and/or a therapeutic compound.

In a preferred embodiment the present invention concerns the avipoxviruses according to the present invention as a vaccine. A "vaccine" is a compound, i.e. a vector or a virus that induces a specific immune response.

The heterologous nucleic acids are preferably inserted into the preferred insertion sites of the viral genome as explained above for the Vaccinia virus host range genes. Thus, preferred insertion sites for heterologous nucleic acids are i.a. intergenic regions of the viral genome, deletion sites and non-essential regions.

If the Avipoxvirus is a non-recombinant virus, i.e. an avipoxvirus that does not contain in the viral genome heterologous genes other than the Vaccinia virus host range gene, the Avipoxvirus can be used to vaccinate against avian poxvirus infections. This is of significant importance in the veterinary field, e.g. for the vaccination of poultry. In this case it is preferred to use an attenuated Avipoxvirus. If the Avipoxvirus is a recombinant virus, i.e. an avipoxvirus that contains in the viral genome heterologous genes other than the Vaccinia virus host range gene, the Avipoxvirus can be used to vaccinate against avian poxvirus infections and/or to induce an immune response against the peptide/protein that is encoded by the additional heterologous nucleic acid. This embodiment is of particular importance if a recombinant Avipoxvirus is used for the vaccination of mammals, in particular humans. In this case the additional heterologous sequence may express antigens against which it is intended to induce an immune response. Examples for such antigens are i.a. tumour antigens, antigens derived from infectious agents such as viruses, bacteria, fungi, synthetic polyepitope strings and so on.

The vaccination is made by administering an Avipoxvirus according to the present invention to an animal, including an human. The mode of administration, the dose and the number of administrations can be optimized by those skilled in the art in a known manner. Most preferred for poxvirus vectors is subcutaneous or intramuscular administration.

For the preparation of a vaccine, the virus according to the invention is converted into a physiologically acceptable form. This can be done based on the experience in the preparation of poxvirus vaccines used for vaccination against smallpox (as described by Stickl, H. et al. [1974] Dtsch. med. Wschr. 99, 2386-2392). For example, the purified virus is stored at $-80°$ C. with a titer of $5 \times 10^8$ TCID$_{50}$/ml formulated in about 10 mM Tris, 140 mM NaCl pH 7.4. For the preparation of vaccine shots, e.g., $10^2$-$10^8$ particles of the virus are lyophilized in phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration. The glass ampoule is then sealed and can be stored between $4°$ C. and room temperature for several months. However, as long as no need exists the ampoule is stored preferably at temperatures below $-20°$ C. For vaccination the lyophilisate can be dissolved in 0.1 to 0.5 ml of an aqueous solution, preferably physiological saline or Tris buffer, and is administered either systemically or locally, i.e. by parenterally, intramuscularly or any other path of administration know to the skilled practitioner.

According to a related embodiment the invention concerns a method for affecting, preferably inducing an immunological response in a living animal body, including a human, comprising administering the avipoxvirus according to the present invention, the pharmaceutical composition and/or or the vaccine according to the present invention to the animal or human to be treated. According to a preferred embodiment the animal may be immuno-compromised. In immuno-compromised animals it is preferred to use severely attenuated virus strains in order to assure that the animal is not overwhelmed by productive virus replication. This may be of particular relevance if the animal is a natural host for the virus, which is the case in poultry. Since Avipoxviruses do not replicate in humans the Avipoxviruses according to the present invention are particularly safe in human beings even if the used virus strain is not an attenuated strain with respect to the natural host.

According to a further embodiment the invention relates to a pharmaceutical composition comprising the avipox virus according to the present invention and a pharmaceutically acceptable carrier, diluent and/or additive. The pharmaceutical composition is in fact a vaccine if the composition comprises an Avipoxvirus containing in the viral genome a heterologous nucleic acid encoding an antigen against which an immune response is to be induced. However, the heterologous nucleic acid is not restricted to this type of sequences. Instead, the heterologous sequence may also be a suicide gene, such as the herpes simplex virus thymidine kinase gene, a therapeutic gene, such as an antisense RNA gene or ribozyme gene or any other gene having an therapeutic benefit. According to the latter alternatives the avipovirus according to the present invention may be part of a pharmaceutical composition aiming at treating disease and not primarily intending to vaccinate against a disease. If the heterologous gene is a suicide gene the pharmaceutical composition may be administered locally to a tumour, leading to the infection of the tumour cells with the recombinant avipoxvirus. The suicide gene is then expressed in the tumour cells and by administration of the prodrug that corresponds to the respective gene product of the suicide gene (e.g. gancyclovir in the case of the Herpes simplex virus thymidine kinase gene) a selective killing of tumour cells becomes possible.

The pharmaceutical composition and/or the vaccine may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

According to a preferred embodiment the invention concerns a method for introducing a homologous and/or a heterologous nucleic acid sequence into target cells comprising the infection of the target cells with the avipoxvirus according to the present invention. In the context of this embodiment the terms "heterologous" and "homologous" nucleic acid refer to nucleic acids which are heterologous and homologous, respectively, with respect to the cellular genome. Thus, according to this embodiment a "homologous nucleic acid" is a sequence which is homolog to the cellular genome, such as a cellular gene or a derivative thereof, having a nucleotide sequence homology in the coding region of at least 50%, preferably of at least 70%, more preferably of at least 80%, most preferably of at least 90%. According to this embodiment the term "heterologous nucleic acid" refers to nucleic acids having no homologue in the cellular genome. Examples for such heterologous nucleic acids are viral, bacterial and fungal genes. The target cell may be any cell that can be infected with the virus according to the present invention.

Thus, the target cell may be an avian cell, such as CEF cells, or mammalian cells, including human cells. The cell may be a primary cell or a cell line. The target cell can be a cell that is cultivated in vitro (i.e. a cell that is cultivated in culture flasks) or a cell that is part of a living organism. Methods how to infect cells are known to the person skilled in the art.

The invention further concerns a method for producing a peptide and/or protein comprising the infection of a host cell with the avipoxvirus according to the present invention, cultivation of the infected host cell under suitable conditions, and isolation and/or enrichment of the peptide and/or protein expressed from the viral genome. The peptide/protein may be a Avipoxvirus protein/peptide. If the Avipoxvirus expresses a nucleic acid which is heterologous to the viral genome, the peptide/protein may also be the peptide/protein that is expressed from the heterologous nucleic acid. The host cell type is not critical as long as the cell can be infected with the virus and as long as the protein/peptide to be isolated is produced in said cell from the viral vector. The cell may be a cell in which the virus replicates productively or a cell that does not promote productive replication such as human cells.

The invention further concerns a method for producing, in particular amplification of the Avipoxvirus according to the present invention comprising the infection of a host cell with the Avipoxvirus according to the present invention, cultivation of the infected host cell under suitable conditions, and isolation and/or enrichment of the virus produced by said host cell. For amplification of the Avipoxvirus it is necessary to infect cells that allow a reproductive replication of the virus. Such cells are known to the person skilled in the art and include avian cells, i.a. CEF cells. Other suitable cells and cell lines have been disclosed above.

The invention further concerns cells infected with the Avipoxvirus according to the present invention. The cells may be cells allowing a productive replication of the Avipoxvirus, such as avian cells, in particular CEF cells or cells that can be infected by the Avipoxvirus but do not promote viral replication, such as primary human cells or human cell lines.

Methods for obtaining the Avipoxvirus according to the present invention are known to the person skilled in the art (see e.g. U.S. Pat. No. 5,766,598; U.S. Pat. No. 5,833,975; U.S. Pat. No. 6,340,462). According to a preferred embodiment such a method may comprise the following steps: In a first step an avipox virus genome and a DNA comprising a host range gene as defined above are introduced into cells in which the virus is able to reproductively replicate. The avipoxvirus genome may already contain heterologous nucleic acids as defined above. The avipoxvirus genome is conveniently introduced into the cell by infection of the cell with the corresponding avipoxvirus. The DNA is preferably introduced in the cell by transfection techniques known to the person skilled in the art. Such techniques include lipofection or Calcium phosphate precipitation. The DNA that is introduced into the cells is preferably capable to specifically recombine with the genomic DNA of the avipoxvirus. To this end the nucleic acid to be inserted into the viral genome is flanked by viral sequences, which direct a specific recombination of the nucleic acid into the viral genome. Depending on the type of the flanking viral sequences it is possible to insert the nucleic acid into any part of the viral genome. Preferably the insertion is done into non-essential regions of the viral genome, into intergenic-regions or into a deletion site.

After the introduction of the viral genome and the DNA comprising a host range gene into cells, virus particles comprising the host range gene in the viral genome are isolated/ enriched from these cells in a second step. Methods for the isolation/enrichment of viral particles are known to the person skilled in the art. These techniques include e.g. the use of marker genes in the nucleic acid sequence that is introduced into the viral genome. If the marker gene is a selection marker (e.g. a resistance gene) only those recombinant viruses that contain the marker will replicate in infected cells under selective pressure (e.g. if an antibiotic is present). Alternatively or additionally color markers (e.g. the green fluorescent protein) could be used. If no selection marker is to be used it is possible to isolate and purify recombinant viruses by limited dilution and/or plaque purification followed by screening of the isolated viruses for the presence of heterologous nucleic acids. Of course these methods may also be combined.

Methods for obtaining an avipoxvirus comprising a Vaccinia virus host range gene and at least one additional heterologous nucleic acid are known to the person skilled in the art and correspond basically to the method for obtaining the Avipoxvirus according to the present invention as described above. Basically there are three preferred alternatives:

According to a first alternative a DNA comprising the at least one additional heterologous sequence and an avipoxvirus genome already comprising an vaccinia virus host range gene in the viral genome are introduced into cells in which the virus is able to reproductively replicate. As pointed out above the DNA is preferably a DNA that is capable to specifically recombine with the genomic DNA of the avipoxvirus. Then viral particles are isolated/enriched that comprise the at least one additional heterologous sequence in the viral genome from these cells. According to a second alternative a DNA comprising a host range gene as defined above and an avipoxvirus genome already harboring the at least one additional heterologous nucleotide sequence are introduced into cells in which the virus is able to reproductively replicate, wherein the DNA is capable to specifically recombine with the genomic DNA of the avipoxvirus. This is again followed by isolating/enriching virus particles comprising the host range gene in the viral genome from these cells. According to the third alternative an avipoxvirus genome and DNA comprising the vaccinia virus host range gene and the additional heterologous nucleic acid sequence are introduced in the cells. The vaccinia virus host range gene and the additional heterologous nucleic acid sequence may be included in one DNA molecule or the host range gene and the heterologous nucleic acid molecule may be included in different DNA molecules. The further steps in the generation of recombinant viruses are as described above.

As pointed out above the inventors have shown that the expression of vaccinia virus host range genes in cells productively infected with an avipoxvirus leads to an increase of the avipoxvirus titer produced from the infected cells. According to the above embodiments the expression of the vaccinia virus host range genes was achieved by including functional vaccinia virus host range genes into the viral genome of the avipoxvirus, wherein the host range gene is under the regulation of the natural promoter sequence, any other suitable Vaccinia virus promoter, or any other promoter functional in avipoxvirus infected cells.

However, the same results can also be achieved if the functional host range gene is provided by the cell that allows productive replication of the Avipoxvirus. The Vaccinia virus host range gene may be any host range gene as defined above. Preferred host range genes are the Vaccinia virus host range genes for human cells, including the vaccinia virus genes C7L, K1L and E3L. Most preferred is C7L. If not stated otherwise all definitions given above, including the definitions of the viruses, promoters, genes, terms also apply for the following embodiments. Also the order of preferred to most preferred embodiments applies to the following section if not indicated otherwise.

Thus, according to a first alternative of this embodiment the invention concerns a cell comprising a Vaccinia virus host range gene or a homologue of said host range gene, wherein the host range gene is not part of a Vaccinia virus genome. The invention further concerns these cells infected with an Avipoxvirus, i.e. the invention further concerns cells comprising an Avipoxvirus genome. The Avipoxvirus that is to be used for the infection of the cells or the genome of the Avipoxvirus that is comprised in the cell may or may not comprise a Vaccinia virus host range gene or a homologue thereof in the viral genome. Preferably the cell comprising the Avipoxvirus genome comprises a Vaccinia virus host range gene or homologue thereof, wherein the host range gene or homologue thereof is neither part of a Vaccinia virus genome nor part of the Avipoxvirus genome.

The host range gene is preferably a host range gene or a homologue thereof as defined above, i.e. preferably a host range gene for human cells more preferably a host range gene selected from E3L, C7L and K1L.

The host range gene may be integrated in the cellular genome. Methods to generate cell lines containing a foreign gene in the cellular genome are known to the person skilled in the art. According to this embodiment the most preferred cell lines in which the vaccinia virus host range gene is to be stably integrated are avian cell lines (see above), in particular QT35 cells. According to the present invention the Vaccinia virus host range gene comprised in the cellular genome is a functional gene as defined above.

Alternatively, the host range gene may be part of a non-integrated DNA. The non-integrated DNA may be a plasmid DNA that has been introduced into the cell by conventional techniques, before or after the cell is infected with the Avipoxvirus. Moreover, the non-integrated DNA may be any DNA that persists in the cell without integrating into the cellular genome. Examples for such a persisting, non-integrating DNA are recombinant viral genomes, such as Herpesviral genomes and vectors derived from Herpesviral genomes. According to this embodiment the cell may be any cell allowing the productive replication of Avipoxviruses, including primary cells such as CEF cells.

The Avipoxvirus may be any Avipoxvirus as defined above, including recombinant Avipoxviruses.

In a second alternative of this embodiment the invention concerns a cell comprising a Vaccinia virus host range gene or a homologue of said host range gene and an Avipoxvirus genome, wherein the host range gene or the homologue of said host range gene may or may not be part of the Avipoxvirus genome. If not indicated otherwise the definitions, the preferred embodiments as well as the order of preferred to most preferred embodiments corresponds to that of the first alternative of this embodiment as shown above. In particular the host range gene may be inserted into the cellular genome or may be part of a non-integrated DNA. However, in addition to the first alternative of this embodiment the second alternative also includes the possibility that the vaccinia virus host range gene or homologue thereof is part of a vaccinia virus genome. Thus, the invention also relates to cells that comprise an Avipoxvirus genome and a Vaccinia virus genome, wherein the Vaccinia virus genome comprises at least one Vaccinia virus host range gene, in particular at least one of the preferred host range genes as defined above. The Vaccinia virus host range genes are expressed and exert a positive effect on the replication of the Avipoxvirus, resulting in an increased amount of Aviopoxvirus produced from said cells compared to cells not comprising a Vaccinia virus genome.

Cells comprising a Vaccinia virus genome as well as an Avipoxvirus genome can be easily obtained by infecting a suitable cell with both, a Vaccinia virus and an Avipoxvirus. If the infected cell allows a productive replication of both, Vaccinia virus and Avipoxvirus, the result of the coinfection is a mixture of both viruses. For most applications it is desirable to obtain an Avipoxvirus preparation without Vaccinia virus contamination. To arrive in such a Vaccinia virus free preparation it is possible either to use specific Vaccinia virus strains that infect the cells but that do not productively replicate in said cells or to use specific cells or cell lines that allow the reproductive replication of the avipoxvirus but not of the Vaccinia virus.

The above defined cells according to both alternatives of the present invention can be used in a method for amplifying an avipoxvirus characterized in that the cells comprising a Vaccinia virus host range gene or a homologue of said host range gene are infected with the avipoxvirus. The cells are cultivated and the viral particles produced by said cells are isolated/enriched. Alternatively it is possible either to introduce the Avipoxvirus in the cell before introducing the Vaccinia virus host range gene or to introduce the Avipoxvirus and the Vaccinia virus host range gene at the same time. The avipoxvirus may be any poxvirus as defined above, more particularly a wild-type Avipoxvirus, an attenuated Avipoxvirus or a recombinant Avipoxvirus lacking a Vaccinia virus host range gene in the viral genome or a wild-type Avipoxvirus, an attenuated Avipoxvirus or a recombinant Avipoxvirus having a Vaccinia virus host range gene in the viral genome Moreover the invention concerns the use of a Vaccinia virus host range gene or an homologue thereof to increase the titer of avipoxviruses produced from avian cells after infection of said cells with said avipoxvirus, wherein the host range gene is expressed in said cells.

Furthermore the invention relates to a method for increasing the titer of avipoxviruses produced from avian cells by infecting cells comprising a Vaccinia virus host range gene or a homologue of said host range gene with said avipoxvirus.

SHORT DESCRIPTION OF THE FIGURES

FIG. 1: Plasmid map of integration vector pBNCaPVX06 The plasmid contain two regions that are homologous to the Canarypox genome (Flank1, corresponding to the sequence of SEQ. ID: No. 3 and Flank 2, corresponding to the sequence of SEQ. ID: NO. 4). These sequences direct the homologous recombination of the sequences located between Flank1 and Flank 2 into the corresponding location of the viral genome. The integration site into the Canarypox virus genome is located between the TK-gene (Thymidine kinase gene) and a gene named Ca.X with unknown function (see FIG. 3). NPTII=neomycin resistance gene (expressed from the PS promoter which is a Vaccinia virus strong synthetic promoter); IRES=internal ribosomal entry site; EGFP=enhanced green fluorescence protein. BsaI=restriction enzyme recognition site for BsaI; prT3=T3 promoter sequence derived from plasmid Bluescript pBSK+ (Stratagene, Inc.); prT7=T7 promoter sequence derived from plasmid Bluescript pBSK+ (Stratagene, Inc.). In this description the designations pBNCaPVX06 and pBNXCaPV06 are used interchangeably and refer to the same plasmid.

Figure 2:
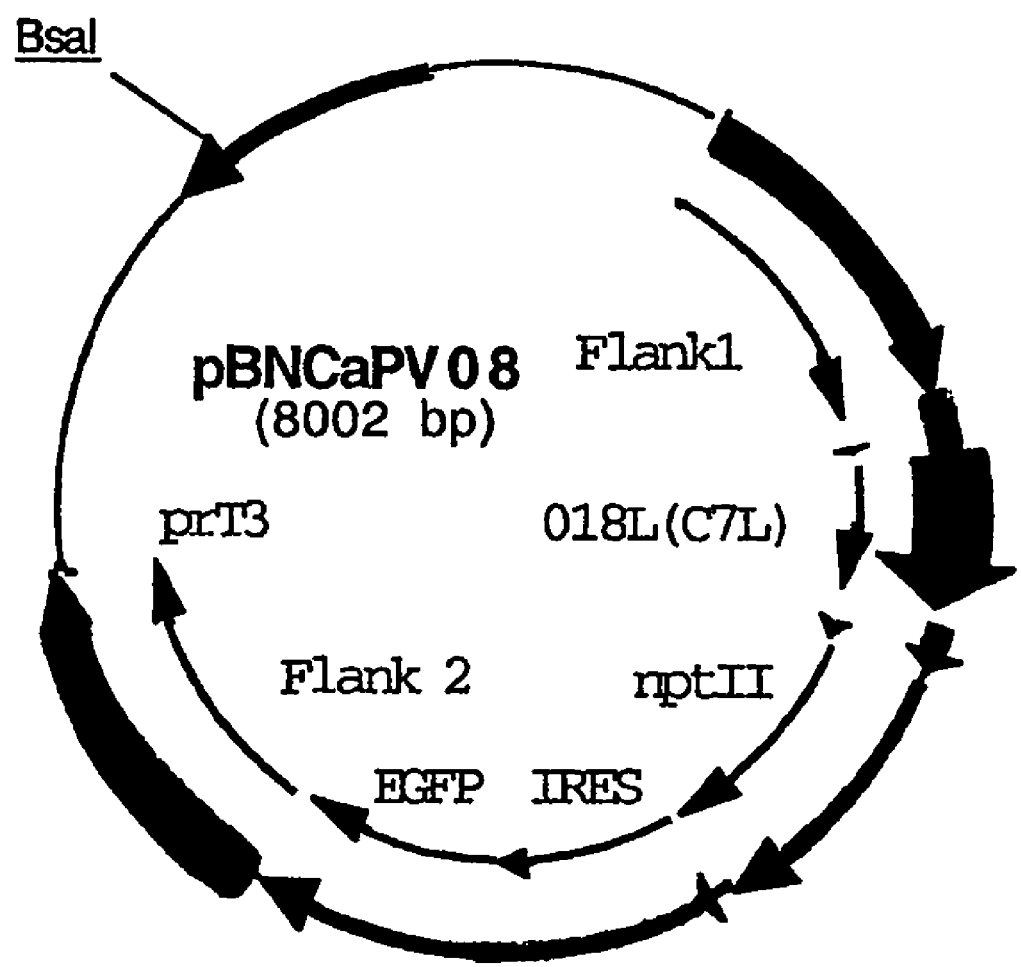

FIG. 2: Plasmid map of integration vector pBNCaPV08 This plasmid basically corresponds to pBNCaPVX06 explained in the legend to FIG. 1. pBNCaPV08 additionally comprises the C7L gene derived from MVA (Modified Vaccinia Ankara) expressed from the natural C7L promoter (see FIG. 4). The C7L gene from MVA shows the same nucleotide sequence than the C7L gene in Vaccinia virus.

FIG. 3: Graphical overview of the intergenic region of the Canarypox genome used for the insertion of Vaccinia virus host range genes. Ca.6, Ca.5, Ca.X, Ca.3: Canarypox virus genes 6, 5, X and 3, respectively; Ca.TK: Canarypox virus Thymidine kinase gene; Flank1 (SEQ. ID: NO. 3) is a DNA fragment comprising parts of the Ca.6 gene, the entire Ca.5 gene and the entire Ca.Tk gene. Flank2 (SEQ. ID: 4) is a DNA fragment comprising the entire Ca.X gene and parts of the Ca.3 gene.

FIG. 4: Sequence of C7L region of MVA (Modified Vaccinia Ankara). This polynucleotide sequence corresponds to SEQ ID NO:1. In addition this polynucleotide sequence expresses an amino acid sequence set forth as one letter amino acids. The amino acid sequence set forth with one letter amino acids has the same structure as the amino acid set forth with three letter amino acids that is SEQ ID NO:2.

Figure 5A:
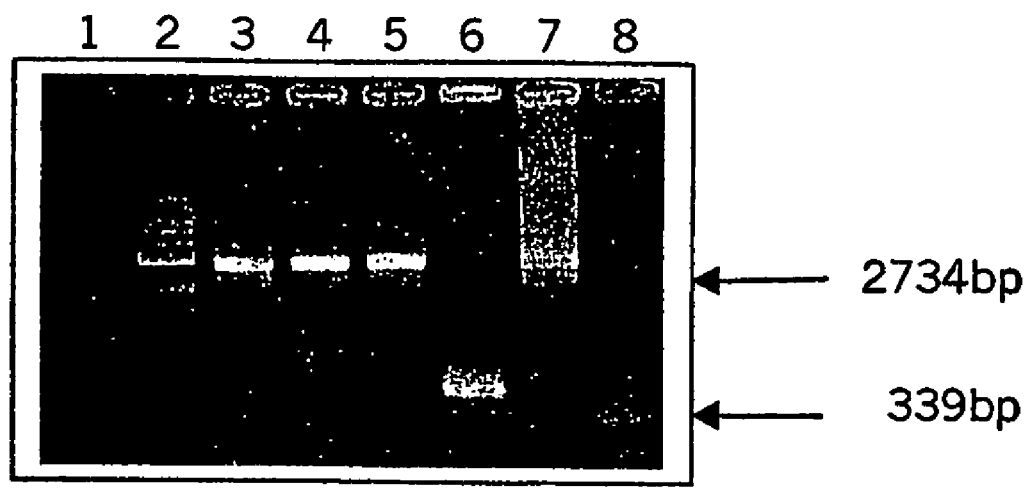
Figure 5B:
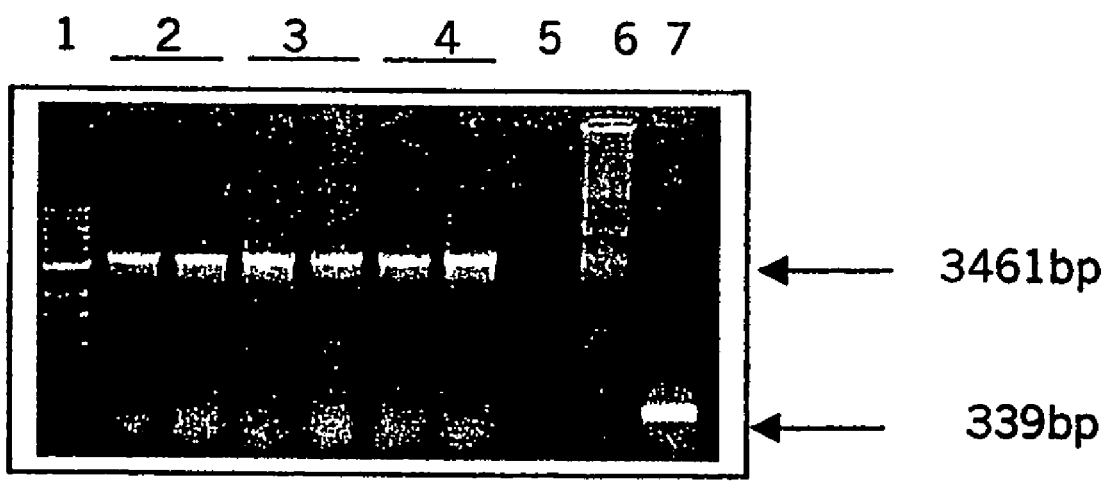

FIG. 5: PCR products for the recombinant Canarypoxviruses canBNX01 and canBN01. FIG. 5A: PCR product for canBNX01 shown on a 0.8% agarose gel. lane 1: 100 bp marker; lane 2: 1 kb marker; lanes 3-5: different canBNX01 isolates; lane 6: CaPV wildtype; lane 7: pBNCaPVX06; lane 8: water control. FIG. 5B: PCR product for canBN01 shown on a 0.8% agarose gel. lane 1: 100 bp marker; lanes 2-4: different canBN01 isolates; lane 5: water control; lane 6: pBNCaPV08; lane 7: CaPV wildtype FIG. 6: Multistep Growth Curve of recombinant CaPV on Various Cell lines. Amplification of canBNX01 (recombinant CaPV comprising the marker gene cassette but not the Vaccinia virus C7L gene) and canBN01 (recombinant CaPV expressing the C7L gene and the marker gene) in the cell lines BHK-21, Vero, 143B, HaCaT, Hela and MRC-5 and in CEF cells. Virus amplification (fold increase in virus yield above the input level in 6-well-plates) was determined by dividing the virus yield at 96 hours by the input of $5\times10^4$ (moi 0.05). A ratio of 1,0 means that output=input. The ratios represent the average values of three experiments. Standard errors are indicated by bars.

FIG. 7: Nucleotide Sequence (SEQ. ID NO. 3) of Flank 1 (part A, above) and of (SEQ. ID NO. 4) Flank 2 Part B, below).

EXAMPLES

Example 1

Construction of Recombinant Canarypox canBNX01 (pS NPTII IRES EGFP) and canBN01 (pS NPTII IRES EGFP C7L-MVA)

Summary:

This example describes the generation of recombinant Canarypox virus using NPTII (neomycin resistance gene) and EGFP (green fluorescent protein) selection. The Vaccinia Virus host range gene C7L was cloned into an intergenic region of Canarypox by homologous recombination. After two plaque purifications (PP) there was no wild type virus detectable but only recombinant virus. Sequencing of the integration region showed proper integration and no mutations. RT-PCR showed successful expression of the integrated genes, namely the C7L gene from Modified Vaccinia Ankara and the marker gene cassette. The recombinant virus was shown to be stable up to passage number twenty, even without the selective pressure of Geneticin®.

Introduction:

The aim of this example was to construct a recombinant Canarypox virus expressing the Vaccinia Virus host range gene C7L plus marker cassette (canBN01) and a recombinant Canarypox expressing the marker cassette alone (canBNX01). Therefore the integration vectors pBNCaPVX06 (see FIG. 1) and pBNXCaPV08 (see FIG. 2) had been cloned. Both contain two flanks homologous to the Canarypox virus genome, a marker cassette (NPTII=neomycin resistance, IRES=internal ribosomal entry site, EGFP=enhanced green fluorescence protein) and for pBNCaPV08 additionally C7L derived from MVA (Modified Vaccinia Ankara) expressed by the natural C7L promoter (see FIG. 4; SEQ ID: No 1). C7L from MVA shows the same nucleotide sequence as C7L in Vaccinia virus. The marker cassette is expressed by PS promoter (Vaccinia strong synthetic promoter). The integration site into the Canarypox virus is located in-between the TK-gene (Thymidine kinase) and a gene named Ca.X with unknown function (see FIG. 3).

| Material: | |
|---|---|
| Recombination vector | pBNCaPVX06 (pBS PS NPT11 1RES EGFP) (FIG. 1) pBNCaPV08 (pBS PS NPT11 1RES EGFP C7L-MVA) (FIG. 2) |
| Cells | CEF (Chicken Embryo Fibroblast) |
| Virus | CaPV crude stock 3.2E+06 $TCID_{50}$/ml |
| Transfection kit | Effectene (Roche) |
| DNA-Extraction | Qiagen Blood DNA Kit (Qiagen) |
| PCR for Wildtype | Taq Polymerase (Roche) Primer: #487: 5'-agcggctttaaatggagatttc-3' (SEQ. ID NO: 5) Primer: #488: 5'-gttattgttcggaatagaagac-3' (SEQ. ID NO: 6) |
| Sequencing | Expand Polymerase (Roche) Big Dye Terminator Kit (PE) |
| Titrations | Anti-CaPV Serum (Guinea Pig #433/1) Anti-Guinea-Pig |
| Reverse Transcriptase | Rneasy Mini Kit (Qiagen) DNAse (Roche) M-MLV RT RNAsin (Promega) Taq Polymerase (Roche) Primer: #504: 5'-ttacttgtacagctcgtccatgc-3' (SEQ. ID NO: 7) #505: 5'-atgggatcggccattgaacaag-3' (SEQ. ID NO: 8) #506: 5'-ggcggcggtcacgaactc-3' (SEQ. ID NO: 9) #498: 5'-ttaatccatggactcataatc-3' (SEQ. ID NO: 10) #496: 5'-tatacagcacgaattcgacatcatta-3' (SEQ. ID NO: 11) #497: 5'-ctatacgggattaacggatgttc-3' (SEQ. ID NO: 12) |

Method and Results:

1. Homologous Recombination (HR):

Plasmids pBNCaPV09 and pBNCaPVX06 (see FIGS. 1 and 2) were linearised with Restriction Enzyme BsaI at 50° C. over night (cuts in the backbone of the plasmids). The digests were purified with a PCR purification kit (Qiagen) and eluted with 50 ul $H_2O$.

CEF cells were seeded into 6-well-plates using RPMI 10% FCS. Next day 60 to 80% confluent cells were infected with CaPV crude stock at a moi of 0.1 and 0.01, respectively. Infection was left for one hour at 37° C., virus suspension was removed, and cells were washed with RPMI and 1.6 ml RPMI 2% FCS were added.

Transfection was carried out using Effectene Kit (Roche) following the instruction manual: linearised plasmid (50 µl) was mixed with 80 µl Buffer EC and 8 µl enhancer were added. The solution was mixed and left for 5 min at room temperature. Then 25 µl Effectene were added, mixed and left for 10 min at room temperature. Finally 600 µl RPMI 2% FCS were added and transferred onto the cells. The transfection was left for four days at 37° C. until fluorescence was detectable. The infection with moi 0.1 seemed to be more effective as clearer fluorescence was detectable. Plates were freeze/thawed three times and finally frozen down at −20° C.

2. Passage and Plaque Purification:

As pointed out above the plasmids used to generate recombinant canarypoxvirus contain a Neomycin resistance gene. Thus, it is possible to select for recombinant viruses by adding Geneticin® at a concentration of 200 µg/ml to the cell culture media.

Preparation of Crude Virus Stock canBNX01:

After transfection/infection (see above) the obtained virus containing suspension was given to fresh CEF cells under selective pressure in 6 well plates. The supernatant of cells in which fluorescent plaques were obtained was used for purification of recombinant virus by limited dilution under selection pressure of Geneticin® and by screening for cells/plaques in which the green fluorescent protein was expressed. The generation of recombinant virus was confirmed by PCR screening which also allowed to detect residual Wildtype contamination. The plaque purification steps were repeated until no Wiltype contamination was detectable by PCR. Nearly confluent T25 flasks of CEF cells were infected with 100 µl supernatant of 3 wells in which positive clones for canBNCaPVX01 were detected that were free of wildtype contamination. The media contained Geneticin®. After three days incubation at 37° C. positive fluorescence and CPE was detectable. Flasks were freeze/thawed three times and a crude stock was harvested (P7=passage number seven). An aliquot of 200 µl was taken for PCR analysis. The remaining material was frozen at −20° C. The following three passages were conducted in T25 flasks of CEF cells with and without selection pressure of Geneticin®. The working crude stocks (P11) were prepared in T175 flasks of CEF cells with and without Geneticin®. After these passages the recombinant virus was shown to be stable without Wildtype contamination even in the passages without Geneticin®.

Preparation of Crude Virus Stock canBN01:

Nearly confluent T25 flasks of CEF cells were infected with 100 µl supernatant of 3 wells in which positive clones for canBNCaPV01 were detected. The further purification was done in the same manner as described above.

3. PCR Analysis of Recombinant Virus and Wildtype

| | |
|---|---|
| DNA | 5.0 µl |
| H20 | 2.95 µl |
| ×10 buffer | 1.0 µl |
| dNTPs | 0.2 µl |
| Primer #487 | 0.4 µl |
| Primer #488 | 0.4 µl |
| Taq Polymerase | 0.05 µl |

PCR Coditions:

94° C., 5 min; 94° C., 30 sec; 53° C., 30 sec; 68°, 3 min; 35 cycles; 68° C., 7 min; 4° C. hold Controls:

pBNCaPVX06 and pBNCaPV08 (plasmids used for integration)

DNA from Canarypox (CaPV) (control for Wildtype)

Water control

Size of Expected PCR-Products:

| | |
|---|---|
| pBNCaPVX06 and recombinant virus (canBNX01): | 2734 bp |
| pBNCaPV08 and recombinant virus (canBNX01): | 3461 bp |
| CaPV: | 436 bp |

The PCR analysis (FIGS. 5A and 5B) has clearly demonstrated that recombinant virus was produced and that the purified viruses were free of input wildtype virus.

4. Sequencing of Inserted Genes

Sequencing was conducted with the ABI Prism sequencing machine according to the manufacturers instructions. A PCR product created with primers #487, #488 and Expand Polymerase was used for sequencing. This PCR product includes partly the integration flanks (F1, F1) and entire NPTII IRES EGFP and C7L regions. The expected sequence could be confirmed.

5. Titration of Crude Stocks canBNX01 and canBN01P11

Virus titers were determined in double titrations and the average titer was calculated as follows:

| | |
|---|---|
| canBNX01 plus Geneticin ®: | 4.9E+06 TCID$_{50}$/ml |
| canBNX01 without Geneticin ®: | 3.7E+06 TCID$_{50}$/ml |
| canBN01 plus Geneticin ®: | 1.3E+07 TCID$_{50}$/ml |
| canBN01 without Geneticin ®: | 2.2E+06 TCID$_{50}$/ml |

6. RT-PCR as Expression Test 6.1 RNA-Preparation

CEF cells were seeded into 6-Well-Plates (5×10$^5$ cells per well DMEM 10% FCS) and infected the following day with 100 μl of canBNX01 and canBN01, respectively. Infection was left for two days until fluorescence was detectable. RNA-Extraction was conducted with Rneasy Mini Kit (Qiagen) according to manufacturers instructions. RNA concentration was measured by OD.

6.2 DNAse Digest for RT-PCR

| | |
|---|---|
| RNA | 25 μl |
| DNAse (RNAse-free) | 3 μl |
| 10 × buffer A (Roche) | 5 μl |
| H$_2$0 (RNAse-free) ad | 50 μl |

90 min at 37° C.

Digest was cleaned up using Rneasy Mini Protocol for RNA Clean up and RNA concentration was measured by OD.

6.3 Reverse Transcriptase

RNA and Primer #504 (for canBNX08) or #498 (for canBN01) were mixed in a ratio of 2 μg RNA to 1 μg primer. Water (RNAse-free) was added up to a total volume of 10 μl. The mixture was left for 5 min at 70° C. and then it was incubated on ice.

The following was added:

| | |
|---|---|
| 5 × buffer | 5 μl |
| dNTP | 5 μl |
| Rnasin | 0.5 μl |
| M-MLV RT | 2 μl |
| H$_2$O (RNAse-free) | 2.5 μl |

60 min 42° C.

RT was cleaned up using PCR purification Kit (Qiagen).

6.4 PCR (Taq Roche)

| | |
|---|---|
| DNA | 5 μl |
| ×10 buffer | 5 μl |
| dNTP | 1 μl |
| Primer 1 | 2 μl |
| Primer 2 | 2 μl |
| Taq (Roche) | 1 μl |

PCR Conditions:
94° C., 5 min; 94° C., 30 sec; 58° C., 30 sec; 68° C., 2 min 30 sec; 30 cycles; 68° C., 7 min; 4° C. hold

| | |
|---|---|
| Samples: | RNA before RT-PCR (to detect contaminant DNA) RNA after RT-PCR and clean up |
| Control: | pBNCaPVX06 and pBNCaPV08 (positive controls) |
| Primer: | #505, #506 for canBNX01 |
| | #496, #497 for canBN01 |

Size of Expected PCR-Products:

| | |
|---|---|
| pBNCaPVX06 and recombinant virus (canBNX01): | 2188 bp |
| pBNCaPV08 and recombinant virus (canBN01): | 428 bp |

The expression of the inserted genes could be confirmed as positive by RT-PCR.

Conclusion:

With the described method it was possible to construct a recombinant Canarypox virus comprising the Vaccinia virus C7L gene. The C7L gene is derived from MVA (Modified Vaccinia Ankara) and shows the same nucleotide sequence as the C7L gene in Vaccinia Virus Copenhagen. The selection method was shown to be very effective since there was no Wildtype virus detectable after two plaque purifications. Sequencing of the inserted genes and parts of the surrounding flanks showed no mutations that affect the function. RT-PCR showed the expression of the Vaccinia host range gene C7L under regulation of the natural promoter.

Example 2

Multistep Growth Curve Analysis of Recombinant Canarypox canBNX01 (pS NPTII IRES EGFP) and canBN01 (pS NPTII IRES EGFP C7L-MVA)

Summary:

The aim of this example was to investigate replication of a recombinant Canarypox virus expressing the human (tissue culture) host range gene C7L under regulation of the natural promoter in a multistep growth curve on several cell lines. Multistep growth curve means that infection is performed on a low moi (multiplicity of infection), which enables to investigate viral spread and replication. The results indicate that the recombinant Canarypox has improved growth properties on CEF cells resulting in titers, which are one log higher than those of the control virus expressing the marker cassette only. The replication properties on several mammalian cell lines (human, monkey and rabbit cell lines) remains non-effected, which means that the recombinant virus seems to be as attenuated as the control virus.

Introduction:

This example evaluates the growth potential of recombinant Canarypox virus expressing C7L (canBN01; for cloning details see example 1) and the control virus not expressing the C7L gene (canBN01; see example 1) in different cell lines or primary cells. The cell lines/cells used are cell that are permissive for the canarypoxvirus, such as CEF cells and cell lines that are non-permissive for the canarypoxvirus, such as BHK-21, Vero, 143B, HaCaT, Hela, MRC-5 and RK-13 cells. Canarypox is known to be strictly restricted to grow only in avian cells as represented by the primary CEF cells (Esposito et al, 1991; Plotkin et al, 1995, Taylor et al, 1995). Unfortunately, the viral titers are relatively low when compared to other poxviruses, for example MVA. Therefore, the growth properties of a recombinant Canarypox virus expressing the human Vaccinia Virus host range gene C7L (Perkus et al, 1990; Oguiura et al, 1993) were evaluated in CEF cells and it was checked whether the recombinant virus is still not capable replicate on mammalian cell lines.

| Material: | |
|---|---|
| Cell lines: | CEF: Chicken Embryo Fibroblast, primary cells<br>BHK-21: Baby Hamster Kidney cells, fibroblast cell line<br>Vero: African green monkey kidney cells, fibroblast cell line<br>143B: human Osteosarcoma cell line, TK<br>HaCaT: human keratinocyte cell line<br>Hela: human cervix carcinoma cell line, epithelial<br>MRC-5: human lung cell line, fibroblast<br>RK-13: rabbit kidney cell line, epithelial<br>All cells are cultured in DMEM 10% FCS |
| Virus: | can BNX01, recombinant Canarypox virus expressing marker cassette only (NPTII, IRES, EGFP; regulated by pS strong synthetic promoter)<br>canBN01, recombinant Canarypox virus expressing marker cassette (NPTII, IRES, EGFP; regulated by pS strong synthetic promoter) and C7L from MVA regulated by the natural promoter |
| Cell Culture Medium: | DMEM plus 2% FCS<br>DMEM, Gibco<br>FCS, PAA |
| Other Reagents: | RPMI, Gibco; Antibiotic-Antimycotic, Gibco; PBS, Gibco<br>Trypsin EDTA (1x), Gibco; Fixing solution: Aceton/Methanol 1:1; Incubation solution: PBS plus 3% FCS; Anti-CaPV Serum (Guinea Pig #433/1); Anti-Guinea-Pig IgG-POD (Sigma); Staining solution: PBS plus TMB (Seramun) 1:1 |

Methods:

Infection of Various Cell Lines in Six-well-plates

Each cell line was grown to nearly confluency in three six-well tissue culture dishes for each of both viruses. The cell monolayers were infected at a moi (multiplicity of infection) of approximately 0.05 using a total of $5\times10^4$ TCID$_{50}$/ml in 500 µl of DMEM for each well. Infection was left for one hour at 37° C., then cells were washed two times with DMEM to remove unadsorbed virus and incubated with 1000 µl DMEM 2% FCS for four days at 37° C. 5% $CO_2$. After the infection the cells were scraped into the medium and cells plus medium were freeze-thawed three times to release the viruses from the cells. These viral extracts were titered on CEF cells.

Titration of CaPV (Immunostaining with a Canarypox Virus Specific Antiserum):

Titration was performed on CEF cells. Briefly, test cells (CEF) were seeded on 96-well-plates in RPMI 1% Antibiotic/Antimycotic 7% FCS at a concentration of $1\times10^4$ cells/well and incubated over night at 37° C. 5% CO2. The test samples had already been frozen/thawed 3 times; dilutions of $10^{-1}$ to $10^{-12}$ were prepared using RPMI medium. Virus dilutions were distributed onto test cells and incubated for five days at 37° C. 5% CO2 to allow CPE development. Test cells were fixed for 10 min, washed with PBS and incubated with poly- clonal Canarypox specific antiserum at a 1:1000 dilution in incubation buffer for one hour at RT. After washing twice with PBS the HPR-coupled anti-Guinea-Pig antibody was added at a 1:1000 dilution in incubation buffer for one hour at RT. Cells were again washed twice with PBS and incubated with staining solution until blue spots were visible (15 min). Staining solution was removed and cells were washed with PBS. Every well showing a brown spot was marked as positive for CPE and titre was calculated using the formula of Kaerber (TCID50 based assay) (Kaerber, G. 1931. Arch. Exp. Pathol. Pharmakol. 162, 480).

Figure 6:
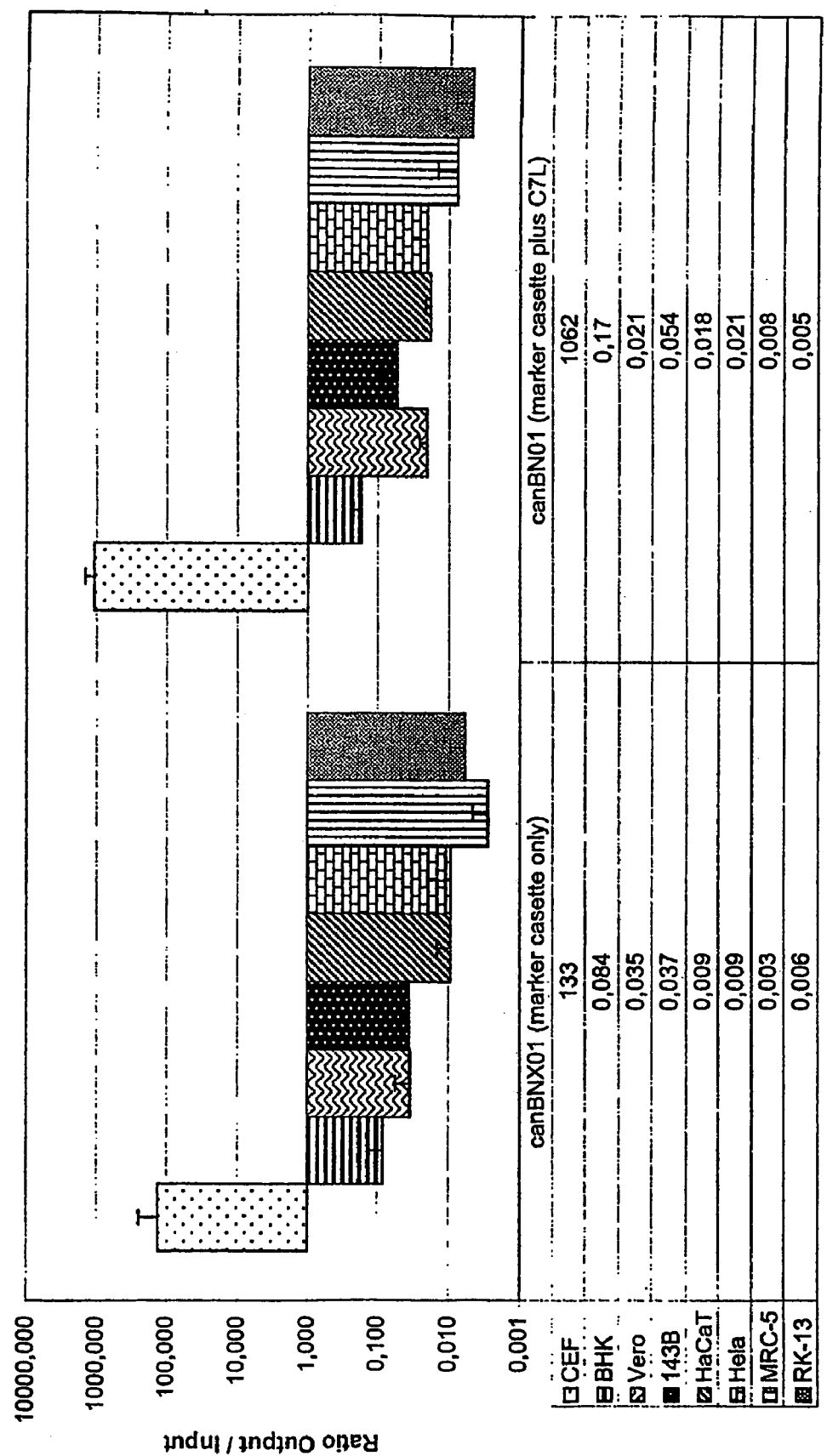

Results:

Recombinant Canarypox virus expressing the Vaccinia Virus host range gene C7L was used to infect triplicate sets of CEF, BHL-21, Vero, 143B, HaCaT, Hela, MRC-5 and RK-13 cells at a low multiplicity of infection (moi 0.05). After infection the virus inoculum was removed and cells were washed two times to remove any unabsorbed free virus particle. Then, infections were left for 4 days; virus extracts were prepared and titrated on CEF cells. FIG. 6 plots the ratios of Output/Input for the 6-well plates (Output means total virus production after four days, and Input means the amount of virus used for the initial infections). These ratios give a clear indication of the extent of viral amplification in the various cell types.

As clearly visible, the recombinant Canarypox expressing C7L (canBN01) shows on CEF cells approximately 10 fold higher titers than the control virus (canBNX01). This means an enhancement of about one log for the titer.

When compared to the level of amplification that occurred in all of the mammalian cell lines tested (100 to 1000 fold decreases above input), canBN01 does seem to be severely growth restricted in the cell lines tested. The expression on a Vaccinia Virus human host range gene does not seem to affect replication of Canarypox on mammalian cell lines. FIG. 6 clearly demonstrates that amplification by cell-to-cell spread of canBN01 in the cell lines tested cannot be detected.

Conclusion:

The genetic engineering of Canarypox resulting in expression of the Vaccinia Virus human host range gene C7L under regulation of its natural promoter (derived from MVA; Modified Vaccinia Ankara) is useful to increase viral titers on CEF cells. Canarypox is known to grow to relatively low titers and to grow slower than the other poxviruses (for example MVA). Therefore, Vaccinia virus host range genes are a good tool to increase the production of Canarypox without affecting the attenuated replication properties on a range of mammalian cells.

REFERENCES FOR EXAMPLE 2

Esposito, J. J. et al.: Arch. Virol. Suppl. (1991) 2, 79-102.
Oguirua, N. et al.: Journal of General Virology (1993) 74, 1409-1413.
Perkus, M. et al.: Virology (1990) 179, 276-286.
Plotkin, S. A. et al.: Dev Biol Stand. Basel, Karger (1995) Vol. 84, 165-170.
Taylor, J. et al.: Vaccine (1995) Vol. 13, No. 6, 439-549.

The invention claimed is:

1. An isolated avian cell, comprising an isolated Vaccinia virus host range gene selected from the group consisting of C18L, C17L, C7L, K1L, B4R, B23R, and B24R or a homologue with at least 90% homology in the coding part of the nucleotide sequence of said host range gene, wherein the host range gene or the homologue of said host range gene is not contained within a poxvirus genome.

2. The isolated avian cell according to claim 1, wherein the host range gene is a Vaccinia virus host range gene selected from the group consisting of C7L, K1L, or a homologue of said host range gene.

3. The isolated avian cell according to claim 2, wherein the host range gene is integrated in the cellular genome.

4. The isolated avian cell according to claim 2, wherein the host range gene is part of a non-integrated DNA.

5. The isolated avian cell according to claim 1, infected with an avipoxvirus grown in avian cells.

6. The isolated avian cell according to claim 5, wherein the avipoxvirus grown in avian cells is a recombinant avipoxvirus.

7. The isolated avian cell according to claim 5, wherein the cells allow the reproductive replication of the avipoxvirus.

8. The isolated avian cell according to claim 1, wherein the host range gene is a Vaccinia virus host range gene C18L, or a homologue of said host range gene.

9. The isolated avian cell according to claim 1, wherein the host range gene is a Vaccinia virus host range gene C17L, or a homologue of said host range gene.

10. The isolated avian cell according to claim 1, wherein the host range gene is a Vaccinia virus host range gene C7L, or a homologue of said host range gene.

11. The isolated avian cell according to claim 1, wherein the host range gene is a Vaccinia virus host range gene K1L, or a homologue of said host range gene.

12. The isolated avian cell according to claim 1, wherein the host range gene is a Vaccinia virus host range gene B4R, or a homologue of said host range gene.

13. The isolated avian cell according to claim 1, wherein the host range gene is a Vaccinia virus host range gene B23R, or a homologue of said host range gene.

14. The isolated avian cell according to claim 1, wherein the host range gene is a Vaccinia virus host range gene B24R, or a homologue of said host range gene.

* * * * *

SEQUENCE LISTING

<160> NUMBER OF SEQ ID NOS: 4

<210> SEQ ID NO 1

```
<211> LENGTH: 615
<212> TYPE: DNA
<213> ORGANISM: MVA
<220> FEATURE:
<221> NAME/KEY: estimated promoter sequence for C7L in MVA
<222> LOCATION: (1)..(162)
<220> FEATURE:
<221> NAME/KEY: CDS
<222> LOCATION: (163)..(615)

<400> SEQUENCE: 1
attaataaac tttaagacat gtgtgttata ctaagatggt tggcttattc catagtagct      60
tgtggaattt ataaacttat gatagtaaaa ctagtaccca atatgtaaag atgaaaaagt     120
aaattactat taacgccgtc ggtattcgtt catccattca gt atg ggt ata cag        174
                                              Met Gly Ile Gln
                                                1 cac gaa ttc gac atc att att aat gga gat atc gcg ttg aga aat tta      222
His Glu Phe Asp Ile Ile Ile Asn Gly Asp Ile Ala Leu Arg Asn Leu
  5              10                  15                  20 cag tta cat aaa ggg gat aac tac gga tgc aaa cta aaa att att tcg      270
Gln Leu His Lys Gly Asp Asn Tyr Gly Cys Lys Leu Lys Ile Ile Ser
                 25                  30                  35 aat gat tac aag aaa tta aag ttt aga ttc att ata cgc cca gat tgg      318
Asn Asp Tyr Lys Lys Leu Lys Phe Arg Phe Ile Ile Arg Pro Asp Trp
         40                  45                  50 tcg gaa atc gac gag gtc aaa gga tta acc gta ttt gca aac aac tat      366
Ser Glu Ile Asp Glu Val Lys Gly Leu Thr Val Phe Ala Asn Asn Tyr
     55                  60                  65 gcg gtg aaa gtt aat aag gta gat gac acg ttc tat tac gta ata tat      414
Ala Val Lys Val Asn Lys Val Asp Asp Thr Phe Tyr Tyr Val Ile Tyr
 70                  75                  80 gag gct gta ata cat ctg tat aac aaa aaa aca gag ata ttg att tat      462
Glu Ala Val Ile His Leu Tyr Asn Lys Lys Thr Glu Ile Leu Ile Tyr
             85                  90                  95                 100 tct gat gat gag aac gaa ctc ttt aaa cac tat tac cca tac atc agt      510
Ser Asp Asp Glu Asn Glu Leu Phe Lys His Tyr Tyr Pro Tyr Ile Ser
                105                 110                 115 cta aat atg att agt aaa aag tat aaa gtt aaa gaa gaa aac tac tca      558
Leu Asn Met Ile Ser Lys Lys Tyr Lys Val Lys Glu Glu Asn Tyr Ser
            120                 125                 130 tcc ccg tat ata gaa cat ccg tta atc ccg tat aga gat tat gag tcc     606
Ser Pro Tyr Ile Glu His Pro Leu Ile Pro Tyr Arg Asp Tyr Glu Ser
        135                 140                 145 atg gat taa                                                          615
Met Asp
    150

<210> SEQ ID NO 2
<211> LENGTH: 150
<212> TYPE: PRT
<213> ORGANISM: MVA

<400> SEQUENCE: 2

Met Gly Ile Gln His Glu Phe Asp Ile Ile Ile Asn Gly Asp Ile Ala
1               5                  10                  15

Leu Arg Asn Leu Gln Leu His Lys Gly Asp Asn Tyr Gly Cys Lys Leu
            20                  25                  30

Lys Ile Ile Ser Asn Asp Tyr Lys Lys Leu Lys Phe Arg Phe Ile Ile
        35                  40                  45

Arg Pro Asp Trp Ser Glu Ile Asp Glu Val Lys Gly Leu Thr Val Phe
    50                  55                  60
```

-continued

```
Ala Asn Asn Tyr Ala Val Lys Val Asn Lys Val Asp Asp Thr Phe Tyr
65                  70                  75                  80

Tyr Val Ile Tyr Glu Ala Val Ile His Leu Tyr Asn Lys Lys Thr Glu
                85                  90                  95

Ile Leu Ile Tyr Ser Asp Asp Glu Asn Glu Leu Phe Lys His Tyr Tyr
            100                 105                 110

Pro Tyr Ile Ser Leu Asn Met Ile Ser Lys Lys Tyr Lys Val Lys Glu
        115                 120                 125

Glu Asn Tyr Ser Ser Pro Tyr Ile Glu His Pro Leu Ile Pro Tyr Arg
    130                 135                 140

Asp Tyr Glu Ser Met Asp
145                 150
```

<210> SEQ ID NO 3
<211> LENGTH: 1001
<212> TYPE: DNA
<213> ORGANISM: Canarypoxvirus

<400> SEQUENCE: 3

```
atactattct tcacggtaca tttaaaaaaa ggaatatagt cagaaacagg aaatatactt      60
tcactataac atggtctaat ttcgaatgtc cgacgttagg agacgttaag tcttcttcac     120
ctaatacctg taatagagta gttttagacg gtagtagata cgttacaaaa acctttaatg     180
atacaatata aatggaacta actagagaaa cgctgatatt tgtaggcatt actgtactag     240
tagtagtaat gatcatatct ggtttctcac taatattgcg attgatacct ggtgtatatt     300
catcagttat tagatcgtcg ttcgtaggag ggaaaatatt aagatttatg gaggtattct     360
ctactgttat gtttatacca tcattagtaa tactttatac agcatatata aggaaatcta     420
aagtgaaaaa taactaaata ttatagtatt tgtaataaat ggctactgga gagattcgtc     480
ttattatagg gcctatgttt tcaggtaaaa caacagaatt agttagatta ataagaagat     540
ttatgatatc gggacgtaaa tgtataataa taaaacattg tagtgattcc cgttataccg     600
aaggagattt agaagctata tatactcatg ataaaatttc gatggaagca ctatcgtgta     660
gcaaattatt acctttaata cctaaaattg ataactttga agtaataggt atagacgaag     720
gacagttttt tgaagatata gtagaattta gtgagattat ggctaataag ggtaaaactg     780
taatcatagc ggctttaaat ggagatttca aacgacaatt atttggaaac atatttaaac     840
tattatcttt atcagaatca gttactagtt taactgctat ttgtgcagtt tgtaaaaacg     900
aagcatcttt ttctaagcgc atgactgatg ataaagatgt aaaagttata ggaggtaaag     960
aaatgtatac tgctgtttgt agaaaatgct tttatgagt c                         1001
```

<210> SEQ ID NO 4
<211> LENGTH: 1003
<212> TYPE: DNA
<213> ORGANISM: Canarypoxvirus

<400> SEQUENCE: 4

```
taatatacgt actaaatact tgtacgtaca actatgttag aataatttgc ttagtatagt      60
atataaacaa gtatgtaaaa aataaaattg atataaaagt agtcttctat tccgaacaat     120
aactatacaa aatggattta gatattaaat cttgcagaag tatttacaaa atatgggata     180
aatatcattt tatgacaggg tataaatata aaaatgataa acagagattt aaaattacaa     240
tttactgtaa atgtgattgt tctatcaaag aatatcctta tagatttgtt actgagaaac     300
```

```
tgcttttaat gtatattatt aataagttta gaggaaagta tctaatcaaa attaggatag      360
aacccatagt taaaaattaa atcatatatc aatacatgtc agtttttat cgaaaaatgg       420 atttataaat aaaatgaaaa ataacttgaa tgaaggaaaa ataaccatg agtaaaaaac       480 cagtaaagac ggtccagcgt agacgtggaa acgatgagga taataagttt acttgtatcc     540
aagcgctaga acatgcaaaa agcttatgta ctaaaaataa taaaatagtt aaatctgtta     600
aactatcaca atctctcttt aagtcatcta acaatatttc tgtgatatta gaaccagaat     660
ataaagacaa attagtgact cctcttatta ttgtagaagg tgaaggaaaa ataccata       720 ataagaatga tagtttttaat cgtgaagaac cgtattttct aaaaatacga cctacgttaa    780
tgaatcctat attatatcag attatggaat gcatttatag agatctcaat tatttggatc    840
ccgagaatac gatggatgaa aaaacattta aagattgtca tctgtatatt aacggaaata    900
ggattatgtc cgccgacgta aaatatttga agaatggtaa acctgtagga gaaaaattat    960
ccgtatccaa ggaaatagat aaactggtta aaaaagatcc aca                       1003
```